(12) United States Patent
DeSalvo et al.

(10) Patent No.: US 8,280,004 B2
(45) Date of Patent: Oct. 2, 2012

(54) SYSTEM AND METHOD FOR NON-DESTRUCTIVE DECONTAMINATION OF SENSITIVE ELECTRONICS USING SOFT X-RAY RADIATION

(75) Inventors: John R. DeSalvo, Satellite Beach, FL (US); Charles M. Newton, Palm Bay, FL (US); William T. Silfvast, Saint Helen, CA (US); Gregory M. Shimkaveg, Oviedo, FL (US)

(73) Assignee: Harris Corporation, Melbourne, FL (US)

( * ) Notice: Subject to any disclaimer, the term of this patent is extended or adjusted under 35 U.S.C. 154(b) by 1309 days.

(21) Appl. No.: 11/986,228

(22) Filed: Nov. 19, 2007

(65) Prior Publication Data

US 2012/0148025 A1 Jun. 14, 2012

Related U.S. Application Data

(63) Continuation of application No. 11/699,443, filed on Jan. 29, 2007, now Pat. No. 7,580,506.

(51) Int. Cl.
*G21K 5/08* (2006.01)
(52) U.S. Cl. .......................................... 378/68
(58) Field of Classification Search .................. 378/64, 378/65, 140, 143, 138; 422/22
See application file for complete search history.

(56) References Cited

U.S. PATENT DOCUMENTS

| 2,922,060 | A | 1/1960 | Rejewsky | |
|---|---|---|---|---|
| 6,738,451 | B2 * | 5/2004 | Avnery | 378/64 |
| 7,447,298 | B2 * | 11/2008 | Busta et al. | 378/122 |
| 2006/0153329 | A1 | 7/2006 | Elyash | |
| 2007/0189459 | A1 | 8/2007 | Eaton et al. | |

FOREIGN PATENT DOCUMENTS

| JP | 1227338 | 9/1989 |
|---|---|---|
| WO | 00/71173 | 11/2000 |
| WO | 02/053195 | 7/2002 |
| WO | 02/075771 | 9/2002 |
| WO | 2008/134099 | 1/2008 |

* cited by examiner

*Primary Examiner* — Irakli Kiknadze
(74) *Attorney, Agent, or Firm* — Harness, Dickey & Pierce, PLC

(57) ABSTRACT

A method is provided for decontaminating biological pathogens residing in an enclosure of an electronic device. The method includes: identifying materials used to encase the enclosure of the electronic device; tailoring x-ray radiation to penetrate the materials encasing the enclosure; and directing x-ray radiation having a diffused radiation angle towards the electronic device.

19 Claims, 6 Drawing Sheets

SYSTEM AND METHOD FOR NON-DESTRUCTIVE DECONTAMINATION OF SENSITIVE ELECTRONICS USING SOFT X-RAY RADIATION

CROSS-REFERENCE TO RELATED APPLICATIONS

This application is a continuation of U.S. patent application Ser. No. 11/699,443 filed on Jan. 29, 2007. The disclosure of the above application is incorporated herein by reference.

FIELD

The present disclosure relates generally to decontamination of biological hazards and, more particularly, to a system and method for non-destructive decontamination of sensitive electronic equipment.

BACKGROUND

When military personnel conduct missions in contaminated environments, there is an eminent need for a decontamination system for the electronic equipment used to support the missions. The ability to maintain material integrity of sensitive electronic devices is a key attribute of any decontamination system. This is particularly true in view of the high cost associated with such electronic devices. In addition, the decontamination system should be transportable with minimal impact to the mission.

Radiation sterilization is generally much less disturbing than using either reactive oxidizers like chlorine or high temperature autoclaving. For instance, quartz-jacketed mercury lamps emitting 254 nm ultraviolet light are effective surface sterilizers, but unfortunately the light cannot penetrate even a single sheet of paper. In contrast, decontamination by 10 MeV electron beams used by the U.S. Postal Service, causes significant damage to the target and requires expensive and cumbersome fixed infrastructure (facilities, power, and shielding).

Soft x-ray radiation offers an efficient, non-destructive, cold, chemical-free sterilization method. However, there is a need to tailor this approach for decontamination of electronic equipment. The statements in this section merely provide background information related to the present disclosure and may not constitute prior art.

SUMMARY

A method is provided for decontaminating biological pathogens residing in an enclosure of an electronic device. The method includes: identifying materials used to encase the enclosure of the electronic device; tailoring x-ray radiation to penetrate the materials encasing the enclosure; and directing x-ray radiation having a diffused radiation angle towards the electronic device.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
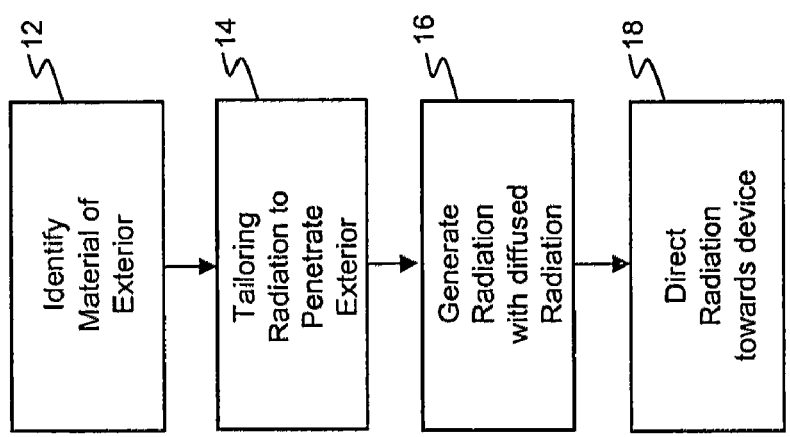
FIG. 1 is a flowchart illustrating an exemplary decontamination technique for electronic equipment.

FIG. 1 illustrates a rapid and non-destructive decontamination technique for electronic equipment. When exposed to a contaminated environment, biological pathogens may penetrate the exterior surface of an exposed piece of electronic equipment. In this case, x-ray radiation may be used to sterilize biological pathogens found in interior compartments of the equipment. It is envisioned that x-ray radiation may be used to sterilize other type of decontaminates which may reside within a piece of electronic equipment.

First, the materials which comprise those parts of the contaminated equipment between its exterior surface and the deepest internal contamination site, and their thicknesses and densities, must be determined as shown at 12. X-ray radiation can then be tailored at 14 to penetrate those materials of the exterior surface of the equipment. X-ray radiation of different photon energies penetrates different materials to different depths. The x-ray transmission, $T_i$, of material I used to construct a piece of equipment is given by $$T_i = e^{-\sigma_i n_i L_i},$$

where $\sigma_i$ is the absorption material's atomic cross section, $n_i$ is the number density (atoms per cubic centimeter), and $L_i$ is the path length that the x-rays follow through the absorption material. For a combination of several layers of different materials, the total transmission is $$T = \prod_i T_i = e^{-\Sigma_i \sigma_i n_i L_i}$$

Each material's atomic cross section is a function of the photon energy. Above the K-shell binding energy, the cross section varies as the inverse square of the photon energy. This strong relationship results in a wide range of transmission T versus energy. An energy level for the x-ray radiation is preferably chosen at which $T = e^{-1}$.

The ideal x-ray photon energy penetrates exactly through the material containing a contaminant, but no more. Use of high energy radiation is wasteful because a preponderance of the incident energy passes through the target without significant energy deposition. On the other hand, very soft x-rays are absorbed by short depths of a material and thus do not penetrate to the location of embedded contaminants. Thus, it is preferable to select the lowest photon energy level needed to pass through the exterior surface of the electronic equipment. For different types of electronic devices, there will be a relatively narrow range of energies which is best suited, matched to the devices mean absorption depth.

Figure 2:
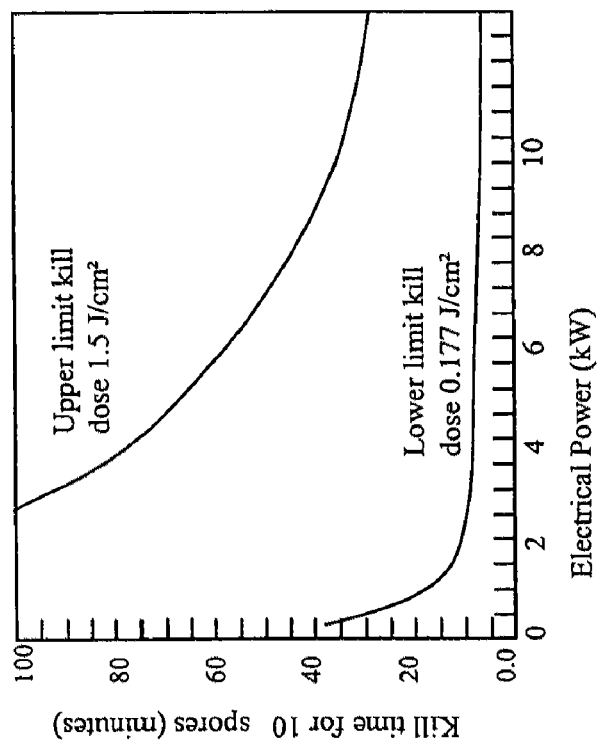
FIG. 2 is a graph illustrating how x-ray radiation having different photon energy levels penetrates polypropylene plastic.

FIG. 2 illustrates an x-ray photon transmission curve for typical plastics (i.e., 2.5 mm of polypropylene plastic). At 5 keV, only a few percent of the radiation penetrates the plastic such that bacteria on the other side of the plastic may survive. At 12 keV, most radiation passes through the plastic without interacting with the bacteria. However, at 8 keV, the radiation effectively penetrates the plastic to kill any embedded bacteria. Therefore, x-ray radiation having a photon energy of 8 keV is preferable for electronic equipment having a plastic exterior surface. For comparison, it has been determined that radiation having 22 keV effectively penetrates one millimeter of aluminum. It is noteworthy that these energy levels are far above the 1.8 keV at which silicon absorbs and thus should not affect the semiconductor components which comprise the equipment. However, the energy levels are low enough that chip packaging will provide some shielding.

Since most electronic devices have varied constituents, it may be more advantageous to use a source spectrum with several sharp peaks. For example, a source may have two peaks in the spectrum—one that penetrates plastic and a second one that penetrates aluminum. This may be achieved with an anode made of an alloy, such as copper-silver or copper-cadmium, or alternatively a patterned plating of higher Z metal on a copper anode. Broad spectrum irradiation like Bremsstrahlung, while always accompanying line radiation to some extent, is inefficient for decomtanmination because the substantial low-energy fraction will not penetrate the target while the high energy tail will pass through and be lost. Compton scattering is mostly negligible at these low energies. In silicon at 8 keV, the photoelectric cross section is almost three orders of magnitude higher than Compton. At 22 keV in carbon, the two cross sections are comparable and will be discussed in relation to the pathogen kill mechanism below.

Figure 3:
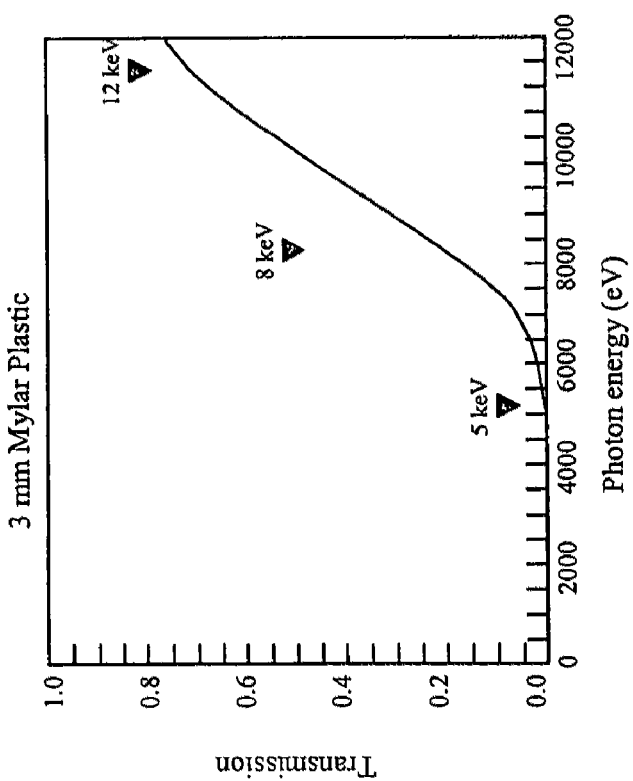
FIG. 3 is a graph illustrating kill times for an exemplary biological pathogen.

When the biological pathogen residing in the equipment is known, the x-ray radiation may be further tailored to sterilize or kill the hazard. For instance, the dose of radiation (i.e., the duration of radiation) applied to the equipment is also determined. The practicality of this concept was demonstrated with a feasibility experiment. Samples of $10^6$ spores of *Bacillus subtilis*, which is a non-hazardous surrogate for *Bacillus anthracis*, were first placed in a test environment and exposed to a dose of x-ray radiation from a copper anode source having photon energies primarily around 8 keV. Irradiated and control samples were then individually incubated in soy broth at 35° C. for a week. Samples with one or more viable spores produce a cloudy infusion, while a completely sterilized sample remains clear. At delivered doses of over 1.5 J/cm$^2$, all samples were completely sterilized. The highest dose delivered to a sample that remained incompletely sterilized was 0.117 J/cm$^2$. Hence the 8 keV x-ray kill dose for $10^6$ spores of our surrogate fell somewhere between those two values. FIG. 3 illustrates the irradiation time required for a complete kill of $10^6$ spores as a function of input electrical power for the upper and lower kill dose bounds. It is well established that killing spores is the most challenging sterilization problem. The radiation dose sufficient to kill bacterial spores is much higher than that required to kill hydrated active bacteria and other biological pathogens. Accordingly, radiation doses for active bacteria and other biological pathogens can be empirically derived in a similar manner.

Figure 4:
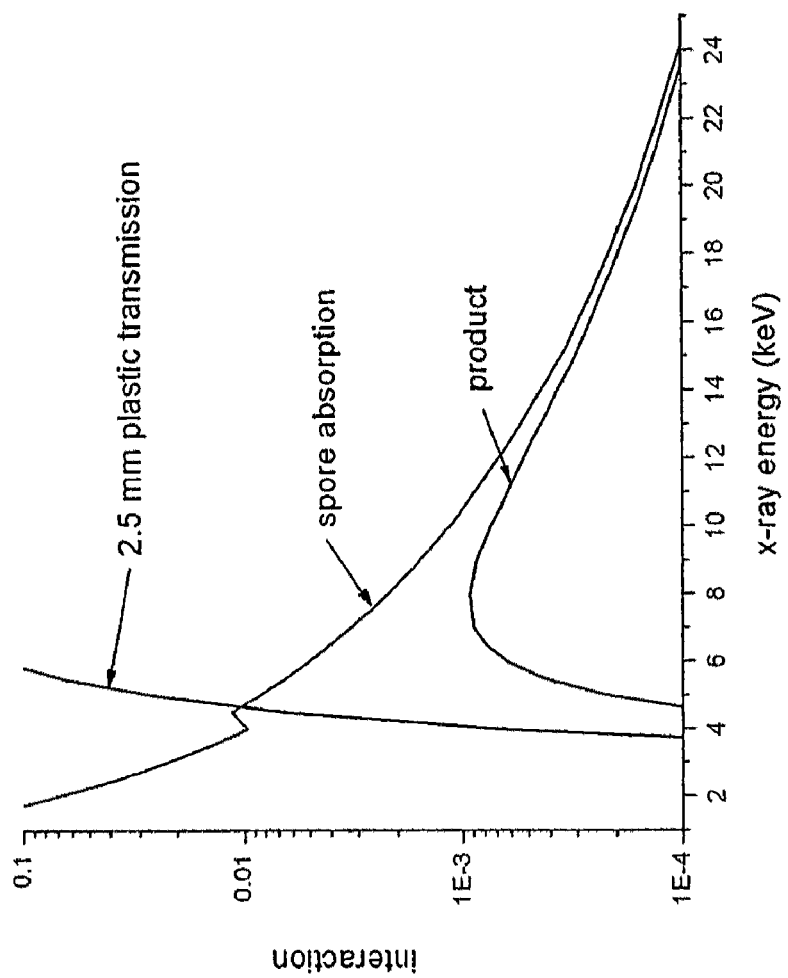
FIG. 4 is a graph illustrating the interaction strength of x-ray radiation with an embedded spore in a plastic environment.

Any radiation that is energetic enough to penetrate centimeters of contaminated environment will necessarily have a low inelastic cross section with an individual spore. Given that, the lower the photon energy, the more likely an interaction with a spore will occur. In fact, the combination of the x-ray requirements of penetrating the spore's surrounding and also being absorbed by the spore results in a band pass curve as shown in FIG. 4. Note the peak of the curve is near the low-energy cut off determined by the contaminated environment x-ray transmission function.

Moreover, the electron produced by a soft x-ray absorption event is ideally suited to deliver a maximum energy transfer to the spore. A bacterial spore (properly referred to as "endospore") is a dormant form that certain bacteria develop when confronted with difficult environmental conditions. It is characterized by a significant water loss (down to 20% or less), concentration of minerals (particularly calcium), formation of a multiple membrane outer coat and effectively ceasing metabolism. When a soft x-ray is absorbed in an endospore, a fast-moving primary photoelectron and a slow recoiling ion are produced. The photoelectron traverses the body of the endospore causing secondary ionizations and producing secondary electrons that travel along their paths. The result is a ballistic trajectory of multiple charge displacements. This damage trail can be lethal to the endospore if it significantly disrupts certain structures such as membranes or critical molecules like DNA. Reactive chemistry can also take place along the ionization trajectory because of all the ions and free radicals produced.

For an 8 keV primary photoelectron, the mean free path in protein is very close to 1 μm, or is almost exactly matched to the size of the endospore. At higher energies, the primary photoelectron will exit the endospore long before depositing its full energy. For instance, at 20 keV, the mean path is around 9 μm. Electrons produced by Compton scattering have the same problem, as Compton is a higher energy process.

Design of the x-ray source for decontamination applications is qualitatively different than for conventional x-ray tubes used for imaging. Importantly, the x-ray emitting area needs to be large so that sharp shadows in the illuminated volume are avoided. If sharp, high contrast shadows occur, microscopic pathogens could escape from the irradiation and circumvent the desired sterilization. Since x-rays are emitted from the outermost few microns of anode material which receives electron bombardment, the electron beam must be diverged and spread evenly to impinge over the full surface of the anode to achieve the largest effective source size. To this end, the electric field guiding the electrons must be crafted to diverge from the cathode and intersect the anode uniformly, to the greatest extent possible. This technique of manipulating the electric field distribution in the x-ray source is referred to herein as "field sculpting".

Figure 5:
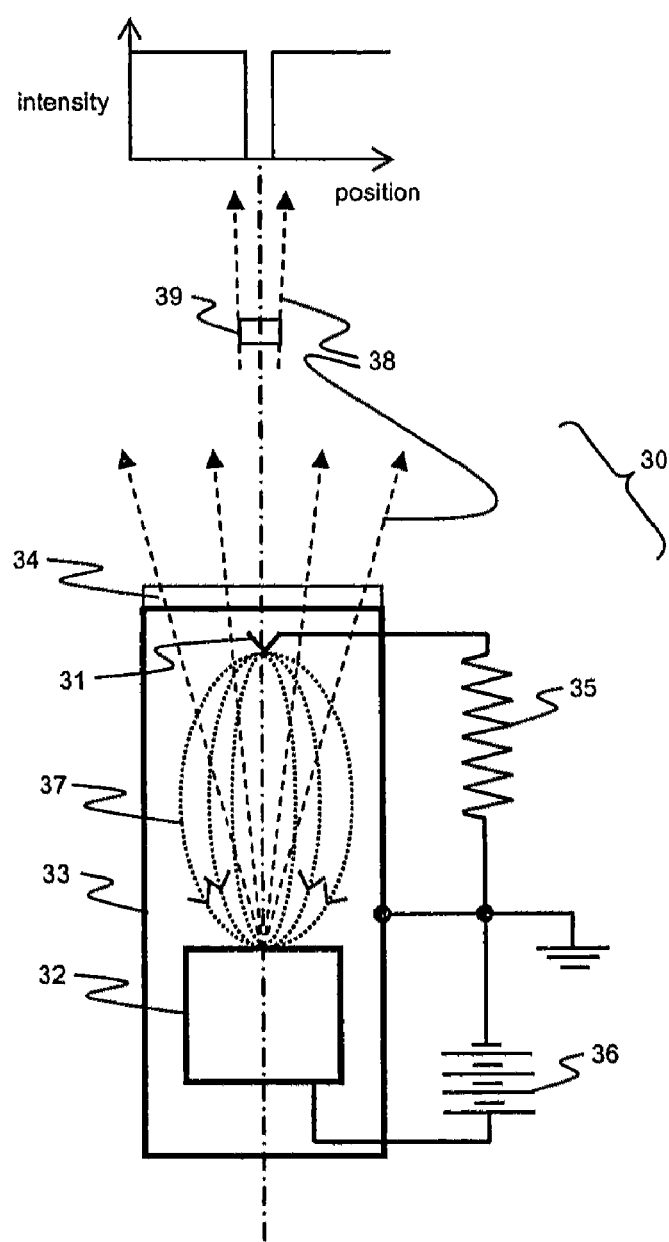
FIG. 5 is a diagram depicting a conventional x-ray source.

Traditional x-ray sources used for imaging applications are designed as point-source emitters as shown in FIG. 5. Briefly, the x-ray source 30 is comprised of a cathode 31 and an anode 32 housed in an electrically conducting, grounded vacuum enclosure 33. The cathode 31 is electrically coupled via a load resistor 35 to a power supply 36. In operation, the cathode emits electrons when energized by the power supply 36. Emitted electrons (paths indicated by dotted lines 37) follow the electric fields and are accelerated towards the anode 32 which in turn emits x-ray radiation 38 (indicated by dashed lines) when the electrons impinge upon its surface. The cathode acquires a voltage (called the self-bias voltage) equal to the product of the load resistance and the emitted electron current. The combination of the cathode's acquired negative voltage, the enclosure ground, and the anode's positive high voltage forms a three-element electron lens, which focuses the electron current density to a small point. All x-ray radiation is generated at that point. Although desirable in imaging applications, this source configuration produces sharp shadows of absorbing materials 39 (which in application would be objects in the contaminated environment such as semiconductor devices, electric leads or wires, for example) as indicated by the plot of intensity versus position behind the absorber. This may obscure the biological hazards and dramatically reduce decontamination efficacy.

Figure 6:
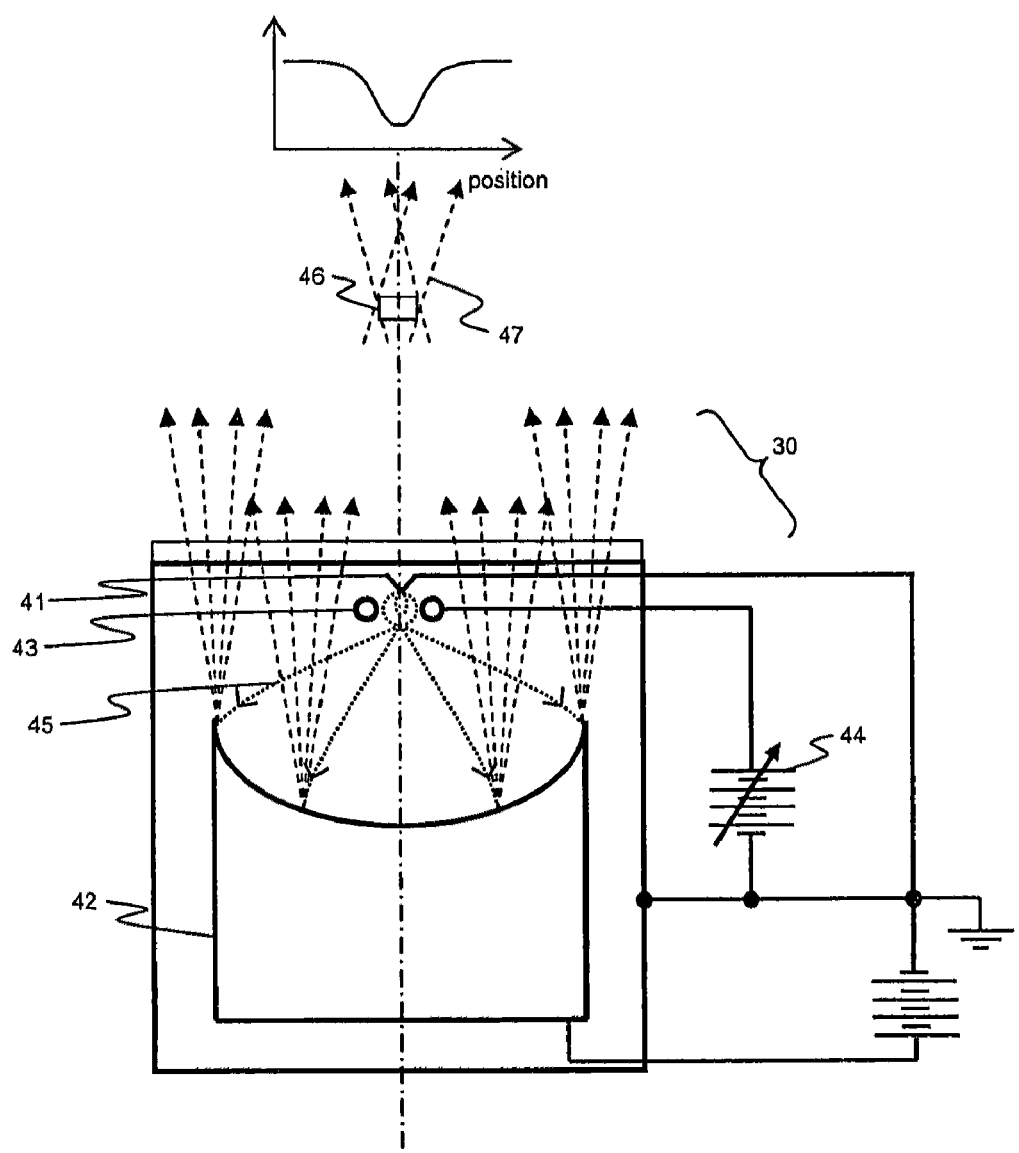
FIG. 6 is a diagram depicting an x-ray source that has been modified to diffuse the radiation.
Figure 8:
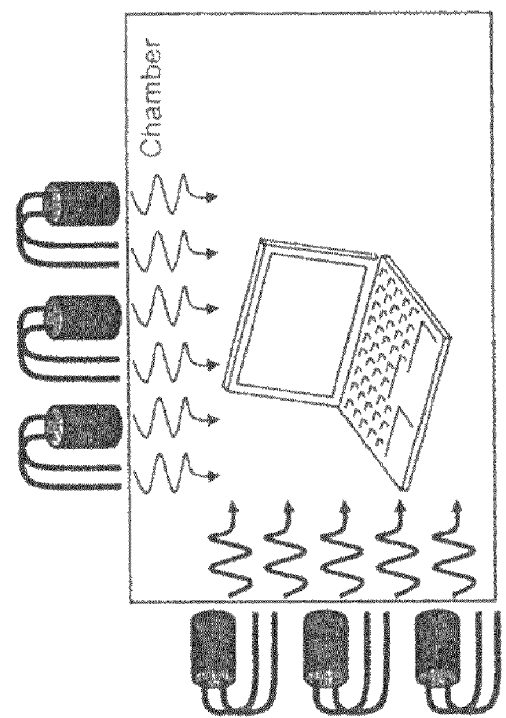
FIG. 8 is a diagram illustrating a decontamination system equipped with multiple types of x-ray heads.
Figure 7:
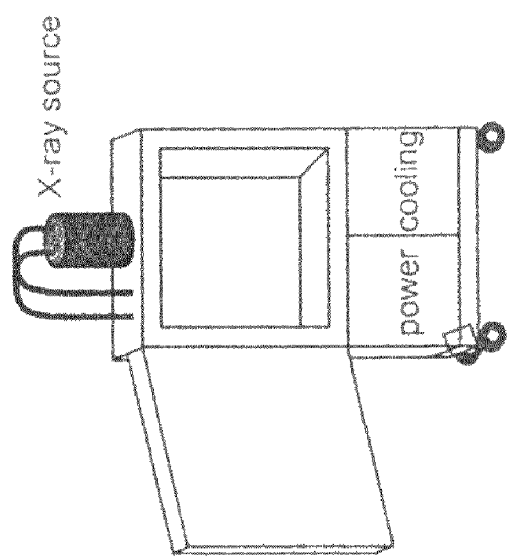
FIG. 7 is a diagram of an exemplary decontamination system.

To make a diffuse x-ray lamp, it is necessary for a large area of the anode surface to emit x-rays. This requires the electron current to be spread wide, avoiding focusing effects. A modified x-ray source design is shown in FIG. 6. Three major modifications have been made to the classical design to accomplish this electron spreading. First, the cathode 41 is electrically tied to ground to avoid any self-bias voltage; the load resistor has been removed. Second, the surface figure of the anode 42 has been curved into a concave shape. Third, a supplementary electrode called the field sculpting electrode 43 is placed surrounding the electron current in close vicinity to the cathode and is biased by a variable voltage 44. Although any one of these changes produces a partial result, the combination of these three changes causes the electric field lines to spread out, drawing the electron current 45 to impact uniformly across the anode surface. In turn, this results in an illumination of the absorber 46 which is diffuse, as indicated by the x-ray trajectories 47. The term "diffused radiation angle" refers to the source possessing the characteristic of a large radiating surface area as viewed by the absorbing material in the contaminated environment, resulting in lowered shadow contrast to avoid having local unirradiated regions. The resulting x-ray intensity pattern behind the absorber does not fall to zero, meaning even if pathogens were to reside behind the absorber they would still be irradiated. The diffused radiation angle may be quantified by a measure analogous to a focal ratio or F-number of a camera. For example, the diffused radiation angle may be measured by an "F-number" defined as the distance from the source to the object being irradiated divided by the size of the x-ray spot. For most conventional x-ray sources, the source size is around 100 microns or smaller, such that its "F-number" is around 10,000. The diffused radiation angle employed by this disclosure gives an "F-number" less than 10 with a final design goal of less than four.

Additionally, this x-ray source may be configured to irradiate over a very wide angle by positioning the output window as close as possible to the anode. X-rays are generated in the first few micrometers of the anode surface that is bombarded with electron current. Any location in the irradiated zone in a clear line of sight to the active anode surface will receive x-rays. The design and location of the output window can be configured to transmit close to a full 2π steradians of irradiated solid angle.

Furthermore, the radiation should thoroughly penetrate the materials covering, surrounding or otherwise obstructing the biological hazard. The x-ray radiation should not pass through the contaminated materials having failed to interact with the biological hazard. High energy x-ray photons will penetrate denser materials, but the resultant scattering cross-section of the photon is low. Therefore, a larger flux of x-ray photons is required, leading to longer exposure times to achieve a sufficient kill dose. This is the reason it is advantageous to choose the x-ray photon energy consistent with the materials needing to be decontaminated.

The photon energies produced by an x-ray source can be scaled through the judicious choice of the anode materials. This is understood through Moseley's empirical formula for k-alpha x-rays. The formula shows the x-ray photon energy is dependent on the square of the atomic number of an element $$E_K \alpha (Z-1)^2$$

where $E_K$ is the x-ray photon energy and Z is the atomic number of the anode material. For instance, an x-ray source having a molybdenum (Z=42) anode will generate radiation having a photon energy of 18 keV. In comparison, a silver (Z=47) anode can generate radiation having a photon energy of 22 keV. It is envisioned that x-ray sources will be fabricated with different anode materials to ensure penetration through various material compositions providing decontamination radiation inside the electronic device. It is also understood that an x-ray source may employ different types of cathodes, including but not limited to thermionic emitters, such as tungsten-thorium alloy, tantalum, and others, as well as cold cathodes which could be metallic wires or exotic materials like carbon nanotubes.

FIG. 7 illustrates an exemplary portable, cart-like decontamination system which may be used to deploy this technology. The decontamination system is comprised of a radiation chamber and one or more x-ray heads arranged to radiate the chamber. Each of the x-ray heads are configured to generate x-ray radiation having a diffused radiation angle in the manner described above. The x-ray head will be made more compact by the use of ultra-high dielectric strength insulators, and weight will be reduced. The vacuum seal will be made permanent. The beryllium window will be shuttered for safety, and interlocks will be installed to prevent operation without radiation shielding.

With reference to FIG. 8, the decontamination system is preferably equipped with multiple x-ray heads. In one exemplary embodiment, different x-ray heads are oriented at different angles within the chamber. In this way, different x-ray heads may be selected to generate x-ray radiation depending upon the object being decontaminated. For example, each of the x-ray heads may employ a copper anode suitable for penetrating plastic materials, but only one of the exterior surfaces of the object is made of plastic. In this example, the x-ray head oriented towards the plastic exterior surface is used to penetrate the object.

In another exemplary embodiment, different x-ray heads may be configured to generate x-ray radiation at different photon energy levels. For instance, one x-ray head may employ a copper anode while another x-ray head employs a silver anode. Thus, different x-ray heads may be used depending on upon the material of the object to be decontaminated. Likewise, different x-ray heads may be used to penetrate different enclosures of the same object, where the different enclosures may be encased by different materials.

X-ray radiation may also be used for decontaminating the exterior surface of electronic equipment. To do so, the portable decontamination system may be equipped with one set of x-ray heads for producing lower energy x-ray radiation (e.g., 8 keV) and another set of x-ray heads for producing high energy x-ray radiation (e.g., 15-30 keV). Lower energy x-rays have larger scattering cross-sections and hence interact strongly with biological pathogens found on an exterior surface of any object. On the other hand, higher energy x-rays are needed to penetrate the exterior surface of the object. Penetrating x-rays may interact with biological pathogens within an enclosure of an object by producing fluorescence. Although the conversion efficiency is low, these photons have scattering cross-sections 900 times larger, thereby achieving effective decontamination within a cavity.

In an alternative configuration, the decontamination system may be equipped with ultraviolet radiation sources for effectuating surface decontamination. Conventional ultraviolet lamps are readily available in the marketplace. Ultraviolet radiation has proven effective for decontaminating and sterilizing biological pathogens. For example, kill doses for UV radiation at 254 nm has been measured. For Bacillus anthracis, doses delivered at 45 $mJ/cm^2$ achieved a 99.9% kill rate of the pathogen on the surface. Doses are low because every photon in absorbed. However, ultraviolet radiation does not penetrate materials. Therefore, x-ray heads are also employed in the manner described above for internal decontamination.

The above description is merely exemplary in nature and is not intended to limit the present disclosure, application, or uses.

What is claimed is:

1. A decontamination system, comprising:
   a chamber adapted to house an object to be decontaminated;
   a first x-ray radiation source arranged to radiate the chamber with x-ray radiation and operable to emit x-ray radiation having a diffused radiation angle and a first photon energy level; and
   a second x-ray radiation source arranged to radiate the chamber x-ray radiation and operable to emit x-ray radiation having a diffused radiation angle and a second photon energy level that is different than the first photon energy level.

2. The decontamination system of claim 1 wherein the x-ray radiation from the first x-ray radiation source is tailored to penetrate an exterior surface of the object and the x-ray radiation of the second x-ray radiation source is tailored to decontaminate the exterior surface of the object.

3. The decontamination system in claim 1 wherein the first x-ray radiation source includes:
   a power supply;
   a cathode electrically connected to the power supply and operable to emit electrons when energized by the power supply; and
   an anode disposed proximate to the cathode and operable to emit x-ray radiation when electrons from the cathode impinge upon an emitting surface thereof, where the emitting surface of the anode is shaped to disperse the x-ray radiation emitting therefrom.

4. The decontamination system of claim 3 wherein the x-ray radiation source includes:
   a power supply;
   a cathode electrically connected to the power supply and operable to emit electrons when energized by the power supply; and
   an anode disposed proximate to the cathode and operable to emit x-ray radiation when electrons from the cathode impinge upon an emitting surface thereof, where the emitting surface of the anode is shaped to disperse the x-ray radiation emitting therefrom.

5. The decontamination system of claim 1 wherein the first x-ray radiation source operable to emit x-ray radiation having a photon energy of approximately 8 keV and the second x-ray radiation source operable to emit x-ray radiation having a phonon energy of approximately 22 keV.

6. The decontamination system of claim 1 wherein the first x-ray radiation source having an anode comprised of a first material and the second x-ray radiation source having an anode comprised of a second material different than the first material.

7. The decontamination system of claim 1 wherein the first x-ray radiation source having an anode comprised of molybdenum and the second x-ray radiation having an anode comprised of silver.

8. A decontamination system, comprising:
   a chamber adapted to house an electronic device to be decontaminated;
   an x-ray radiation source arranged to radiate the chamber with x-ray radiation and operable to emit x-ray radiation having a diffused radiation angle by accelerating electrons from a cathode towards a concave surface of an anode, wherein the x-ray radiation is tailored to penetrate an exterior surface of the electronic device.

9. The decontamination system of claim 3 further comprises a second x-ray radiation source arranged to radiate the chamber with x-ray radiation tailored to contaminate the exterior surface of the electronic device.

10. The decontamination system of claim 8 wherein the first x-ray radiation source operable to emit x-ray radiation at a first photon energy and the second x-ray radiation source operable to emit x-ray radiation at a second photon energy that is different than the first photon energy.

11. The decontamination system of claim 10 wherein the first x-ray radiation source having an anode comprised of a first material and the second x-ray radiation source having an anode comprised of a second material different than the first material.

12. A decontamination system, comprising:
    a chamber adapted to house an object to be decontaminated;
    a first x-ray radiation source having an anode comprised of a first material and arranged to radiate the chamber with x-ray radiation that is tailored to penetrate an exterior surface of the object; and
    a second x-ray radiation source having an anode comprised of a second material and arranged to radiate the chamber x-ray radiation that is tailored to decontaminate the exterior surface of the object, wherein the second material is different than the first material.

13. The decontamination system of claim 12 wherein the first and second x-ray radiation sources are orientated at different angles within the chamber.

14. The decontamination system of claim 12 wherein the first and second x-ray radiation sources are configured to generate x-ray radiation at different photon energy levels.

15. The decontamination system of claim 12 further comprises ultraviolet radiation source arrange to radiate the chamber with ultraviolet radiation.

16. The decontamination system of claim 12 wherein the first x-ray radiation source includes:
    a power supply;
    a cathode electrically connected to the power supply and operable to emit electrons when energized by the power supply; and
    an anode disposed proximate to the cathode and operable to emit x-ray radiation when electrons from the cathode impinge upon an emitting surface thereof, where the emitting surface of the anode is shaped to disperse the x-ray radiation emitting therefrom.

17. The decontamination system of claim 12 wherein the first x-ray radiation source operable to emit radiation at a first photon energy level and the second x-ray radiation source operable to emit radiation at a second photon energy level that is different than the first photon energy level.

18. The decontamination system of claim 17 wherein the first x-ray radiation source operable to emit x-ray radiation having a photon energy of approximately 8 keV and the second x-ray radiation source operable to emit x-ray radiation having a photon energy of approximately 22 keV.

19. The decontamination system of claim 12 wherein the first x-ray radiation source having an anode comprised of molybdenum and the second x-ray radiation having an anode comprised of silver.

* * * * *